United States Patent
Hornegger et al.

(10) Patent No.: US 8,126,902 B2
(45) Date of Patent: Feb. 28, 2012

(54) OPERATING METHOD FOR A COMPUTER HAVING SEQUENCES OF DATA SETS CHANGING OVER TIME AND CORRESPONDING DEVICES

(75) Inventors: Joachim Hornegger, Effeltrich (DE); Dietrich Paulus, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1000 days.

(21) Appl. No.: 11/294,783

(22) Filed: Dec. 6, 2005

(65) Prior Publication Data
US 2006/0123002 A1    Jun. 8, 2006

(30) Foreign Application Priority Data
Dec. 8, 2004 (DE) .......... 10 2004 059 182

(51) Int. Cl.
*G06F 7/00* (2006.01)
*G06F 17/30* (2006.01)
*G06K 9/32* (2006.01)
(52) U.S. Cl. .......... 707/758; 707/941; 382/294
(58) Field of Classification Search .......... 707/758, 707/941; 382/294
See application file for complete search history.

(56) References Cited

U.S. PATENT DOCUMENTS
6,032,678 A * 3/2000 Rottem .......... 600/437
6,447,456 B1 * 9/2002 Tsubata .......... 600/455
6,523,468 B1 * 2/2003 Loffler et al. .......... 101/211
2004/0071367 A1 * 4/2004 Irani et al. .......... 382/284
2004/0167395 A1 * 8/2004 Behrenbruch et al. .......... 600/420

FOREIGN PATENT DOCUMENTS
DE    102 14 763 A1    10/2003
EP    0840253 A2    5/1998
JP    06125499 A    5/1994
WO    03083777 A2    10/2003

OTHER PUBLICATIONS

Josien P.W. Pluim, J.B. Antoine Maintz and Max A. Viergever; "Mutual Information Based Registration of Medical Images: A Survey"; IEEE Transactions on Medical Imaging, 2003, pp. 1-21, vol. XX, No. Y.
J.B. Antoine Maintz and Max A. Viergever; "A Survey of Medical Image Registration"; Medical Image Analysis; 1998; pp. 1-36; vol. 2, No. 1; Oxford University Press.

* cited by examiner

*Primary Examiner* — John R. Cottingham
*Assistant Examiner* — Mariela Reyes

(57) ABSTRACT

Two sequences of data sets having at least two dimensions and referring to an object which changes over time are specified to a computer. Each data set in each sequence is assigned a measure of time which can be used to determine the temporal relationship of the data sets to the other data sets in the respective sequence. The computer compares the first data set) in the first sequence with the data sets in the second sequence and automatically determines a first data set from the second sequence corresponding to a first data set from the first sequence. With the aid of the corresponding first data sets in the first and second sequences and the measures of time assigned to the data sets, the computer then determines, for each of the other data sets in the first sequence, the corresponding data set from the second sequence.

14 Claims, 5 Drawing Sheets

OPERATING METHOD FOR A COMPUTER HAVING SEQUENCES OF DATA SETS CHANGING OVER TIME AND CORRESPONDING DEVICES

CROSS REFERENCE TO RELATED APPLICATION

This application claims priority of the German application No. 10 2004 059 182.2 DE filed Dec. 8, 2004, which is incorporated by reference herein in its entirety.

FIELD OF THE INVENTION

The present invention relates to an operating method for a computer.

BACKGROUND OF THE INVENTION

The present invention further relates to a data medium on which is stored a computer program for executing such an operating method. The present invention further relates to a computer having bulk storage in which a computer program is stored so that the computer executes such an operating method when the computer program is called.

A number of established methods exist for the registration and merging (joint display) of static data sets having at least two dimensions, such as images or volume data sets. Said methods are implemented on computers, and have been put into practice in a plurality of disciplines, particularly in the area of medical technology.

However, medical technology includes not only static data sets but also sequences of such data sets. Such sequences occur for example when recording heartbeats or in the thoracic region during respiratory procedures.

DE-A-102 14 763 discloses an operating method for a computer, which enables the automatic assignment of corresponding pairs of data sets from two sequences of such data sets. Said assignment is determined by evaluating ECG traces associated with the data sets.

JP-AA-06 125 499 discloses an operating method for a computer to which a data set and a sequence of data sets are specified. In this case the data sets are images of an object which changes over time. By comparing the first data set with the data sets in the sequence of data sets, the computer automatically determines a data set from the second sequence that corresponds to the first data set.

SUMMARY OF THE INVENTION

The object of the present invention is to create an operating method for a computer and corresponding elements, in order to create a further capability for determining the corresponding pairs of data sets at least to a large extent automatically in a way which is capable of being applied more widely.

This object is achieved by means of the elements specified in the individual claims.

According to the invention a first sequence of data sets and a second sequence of data sets are specified to the computer, said data sets being images or volume data sets of an object which changes over time. Each data set in each sequence is assigned a measure of time which can be used to determine the temporal relationship of said data set to the other data sets in the sequence concerned. The computer first compares the first data set in the first sequence with the data sets in the second sequence and automatically determines a first data set from the second sequence corresponding to a first data set from the first sequence. With the aid of the corresponding first data sets in the first and second sequences and the measures of time assigned to the data sets the computer then determines, for each of the other data sets in the first sequence, the corresponding data set from the second sequence.

According to the invention, therefore, the corresponding pairs of data sets are determined in two stages, that is, by first of all determining a first mutually corresponding pair of data sets independently of the measure of time, and then using said pair of data sets and the measures of time to determine the remaining mutually corresponding pairs of data sets. In order to determine the first pair of data sets, the first data set in the first sequence and the data sets in the second sequence are checked for similarity. If a measure of the similarity between one of the data sets in the second sequence and the first data set in the first sequence exceeds a threshold, this data set in the second sequence is defined as the corresponding data set. It is of course also possible for the most similar of the data sets in the second sequence to be defined as the corresponding data set.

If necessary it is possible for the computer to determine registration parameters of the first data set in the first sequence and of the data sets in the second sequence relative to one another and then to make use of these registration parameters in determining the first data set of the second sequence that corresponds to the first data set of the first sequence. Fully automatic methods for determining said registration parameters are known: see for instance Pluim, J. P. W., Maintz, J. B. A., Viergever, M. A. (2003), "Mutual-information-based registration of medical images: a survey", IEEE Transactions on Medical Imaging 22, pages 986 to 1004. However it is also possible for registration parameters to be defined interactively or semi-automatically. Methods of this kind are also generally known. An example of this is Maintz, J. B. A., Viergever, M. A. (1998), "A survey of medical registration", Medical image analysis 2 (1), pages 1 to 36.

In many cases the first data set in the first sequence is assigned an additional item of information which differs from the measure of time in that it characterizes the status of the object. Furthermore in these cases such an additional item of information is also assigned to at least one of the data sets in the second sequence. If said object is a heart, the additional information may be cardiac current signals or ECG pulses.

Frequently the object is one which changes periodically. In such cases therefore, the object changes with a first period according to the data sets in the first sequence, and with a second period according to the data sets in the second sequence. The periods may in fact be the same, but this need not be the case and they may therefore be unequal. For instance it is possible to imagine a heart that beats at a rate of 60 beats/minute when the data sets in the first sequence are recorded and at a heart rate of 70 beats/minute when the data sets in the second sequence are recorded. In such cases the measures of time in the first and second sequences are preferably directly related to the first or second period. If this is not the case, the computer must take the periods in the sequences into account when determining which of the data sets in the second sequence correspond to the various data sets in the first sequence.

A possible way for the computer to take the periods of the frequencies into account is first of all to determine, for each data set in the first sequence, a first phase position relative to the first period in each case. The computer should then preferably determine from the second sequence a data set having a second phase position relative to the second period that corresponds at least in some respects, and should define said data set as the corresponding data set. This method is always used when the phase positions of the corresponding data sets are actually equal or differ only slightly from one another. It can also be used when the phase positions differ from one another. This situation is known as nearest interpolation. Depending on the position in each individual case, nearest interpolation can give better results than if the computer were to determine from the second sequence two data sets being immediately consecutive in time and having second phase positions which bisect the first phase position, and if the computer used an interpolation of the said two immediately consecutive data sets from the second sequence to determine an interpolated data set and were to define this as the corresponding data set. However, this last-mentioned method, which is known as true interpolation, is also conceivable and possible. As already indicated, it all depends on the position in each individual case.

With regard to mutually corresponding data sets the computer as a rule also determines their registration parameters. However, if this takes place at an earlier stage, when the first mutually corresponding pair of data sets is being determined, there is obviously no need to determine the registration parameters again at a later stage.

As a rule the computer displays mutually corresponding data sets simultaneously via an output device. Alternatively the traces can be displayed side by side or overlaid within one another according to choice.

It is possible that the computer may determine the mutually corresponding data sets in the first and second sequences with the aid of subsets of the data sets in the first and second sequences. This method can prove effective if the object has changed noticeably in the time between recording the data sets in the first sequence and recording the data sets in the second sequence. For example a lengthy interval may have elapsed between capturing the data sets in the first and second sequences, during which time a pathological change may have taken place in the object. By selecting appropriate, unchanged sub-ranges it is then possible to determine the corresponding pairs of data sets more reliably than by using all of the data sets.

It is possible for the computer to determine the data subsets itself. As a rule, however, the user specifies them to the computer. For example the user can specify hidden ranges to the computer, and the computer can then determine the data subsets from the data sets by subtracting the hidden ranges.

When specifying data subsets or hidden ranges, it is often the case that the only relevant ranges are those hidden ranges in which the changes actually took place. It is therefore possible for the computer to display only the data subsets, or only the differences between the data subsets and the data sets (i.e. the hidden ranges), or even the data subsets and the differences between the data subsets and the data sets (i.e. the hidden ranges) separately from one another.

The data sets in the sequences are mostly either all images or all volume data sets. However it is also possible for the data sets in one of the sequences to be images and the data sets in the other sequence to be volume data sets.

BRIEF DESCRIPTION OF THE DRAWINGS

Further features and advantages of the invention will emerge from the description which follows of embodiments and from the accompanying drawings. These are schematic diagrams which show the following:

FIG. 1 A block diagram of a computer,
FIG. 2 A flow chart,
FIGS. 3 to 6 In each case schematic diagrams of a first and a second sequence of data sets, and
FIGS. 7 to 9 Flow charts.

DETAILED DESCRIPTION OF THE INVENTION

Figure 1:
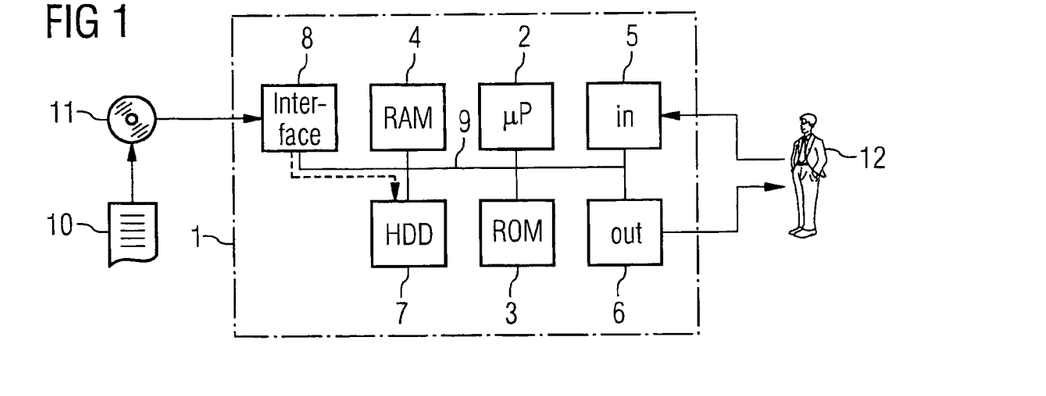

According to FIG. 1 a normal computer 1 has normal components 2 to 9. These components 2 to 9 are a processor unit 2, a read-only memory or ROM 3, a working memory or RAM 4, an input device 5, an output device 6, a bulk storage 7 and a data medium interface 8, said components being interconnected via a bus system 9.

A computer program 10, which has been previously stored in exclusively machine readable form on a data medium 11, can be stored in the bulk storage 7 of the computer 1 via the data medium interface 8. When the computer program 10 has been stored in the bulk storage 7, the computer program 10 can be called by a user 12 with the aid of appropriate call commands. When the computer program 10 is called, the computer 1 executes an operating method which is explained in detail below in conjunction with FIG. 2.

Figure 2:
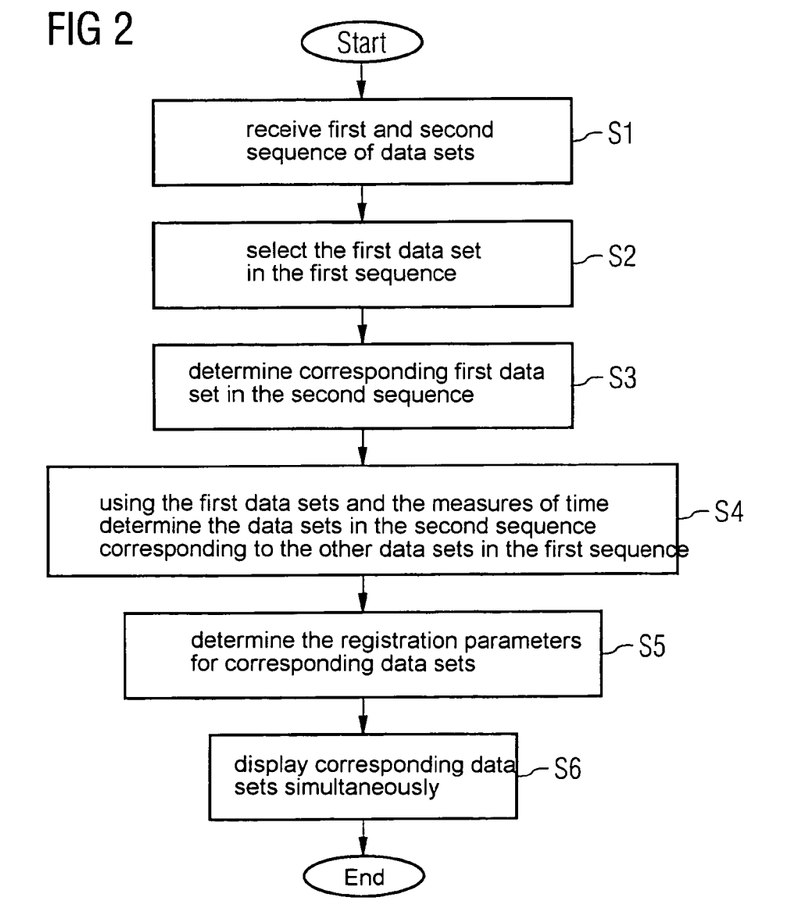

According to FIG. 2, in a step S1 a first sequence 13 of data sets 14 and a second sequence 15 of data sets 16 are first of all specified to the computer 1. In this case the data sets 14, 16 are data sets 14, 16 of an object 17, for example a heart 17, which changes over time.

Figure 3:
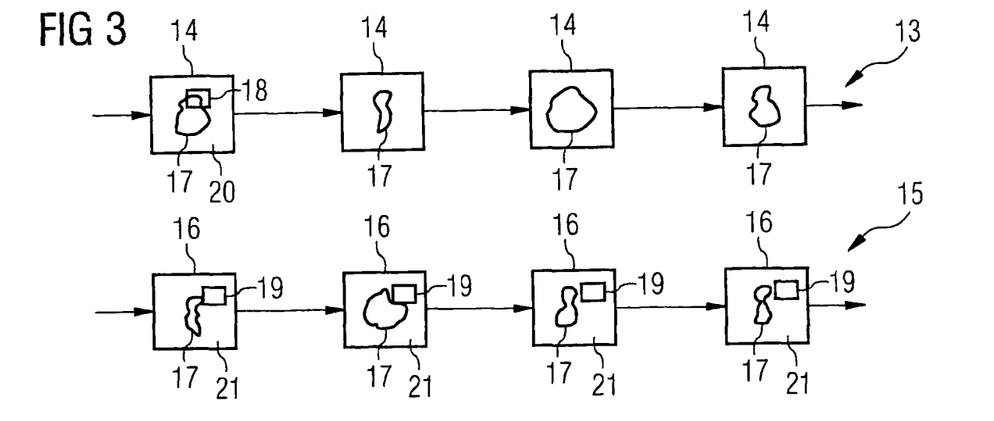
Figure 4:
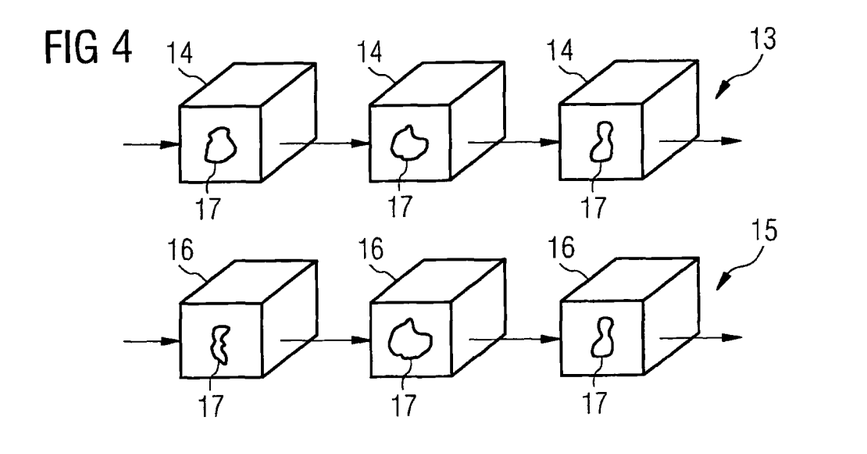
Figure 5:
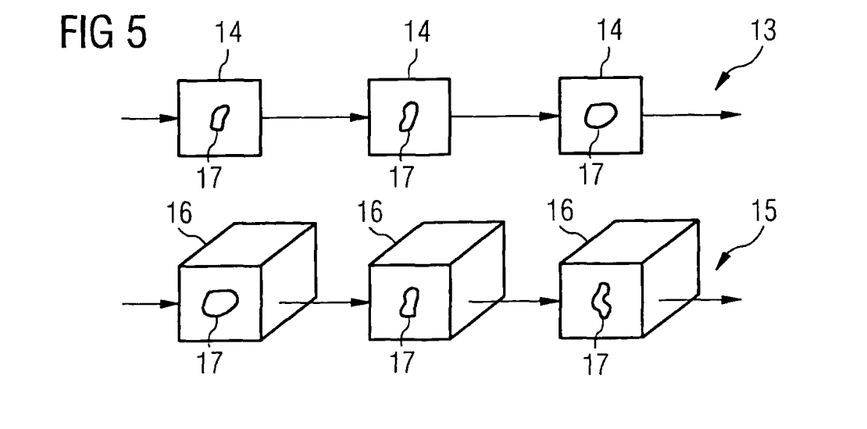

The data sets 14, 16 in the sequences 13, 15 are images 14, 16 (see FIG. 3). Alternatively they can also be volume data sets 14, 16 (see FIG. 4). FIG. 5 shows that mixed forms, in which one of the sequences 13, 15 has images and the other has volume data sets 14, 16, are also possible. Which of the sequences 13, 15 has the images and which has the volume data sets 14, 16 is of minor significance in the context of the present invention.

Figure 6:
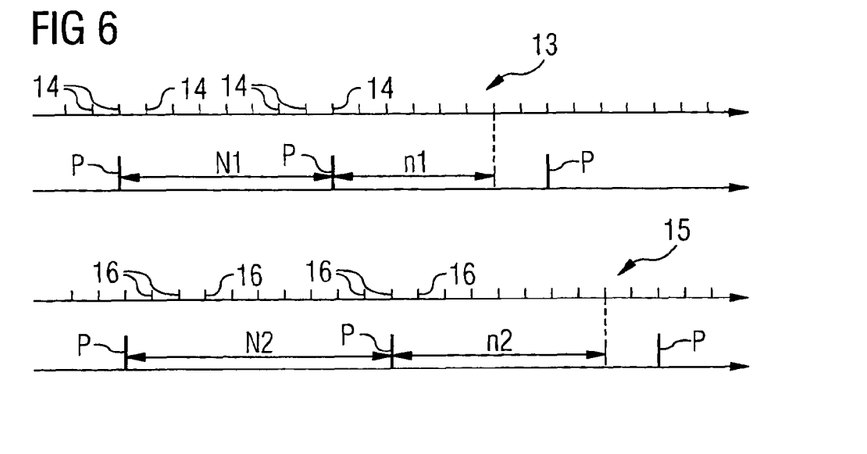

As shown in FIG. 6, each data set 14, 16 in each sequence 13, 15 is assigned a measure of time. Said measure of time can be used within the respective sequence 13, 15 to determine the temporal relationship of a data set 14, 16 to the other data sets 14, 16 in the sequence 13, 15 concerned.

Figure 8:
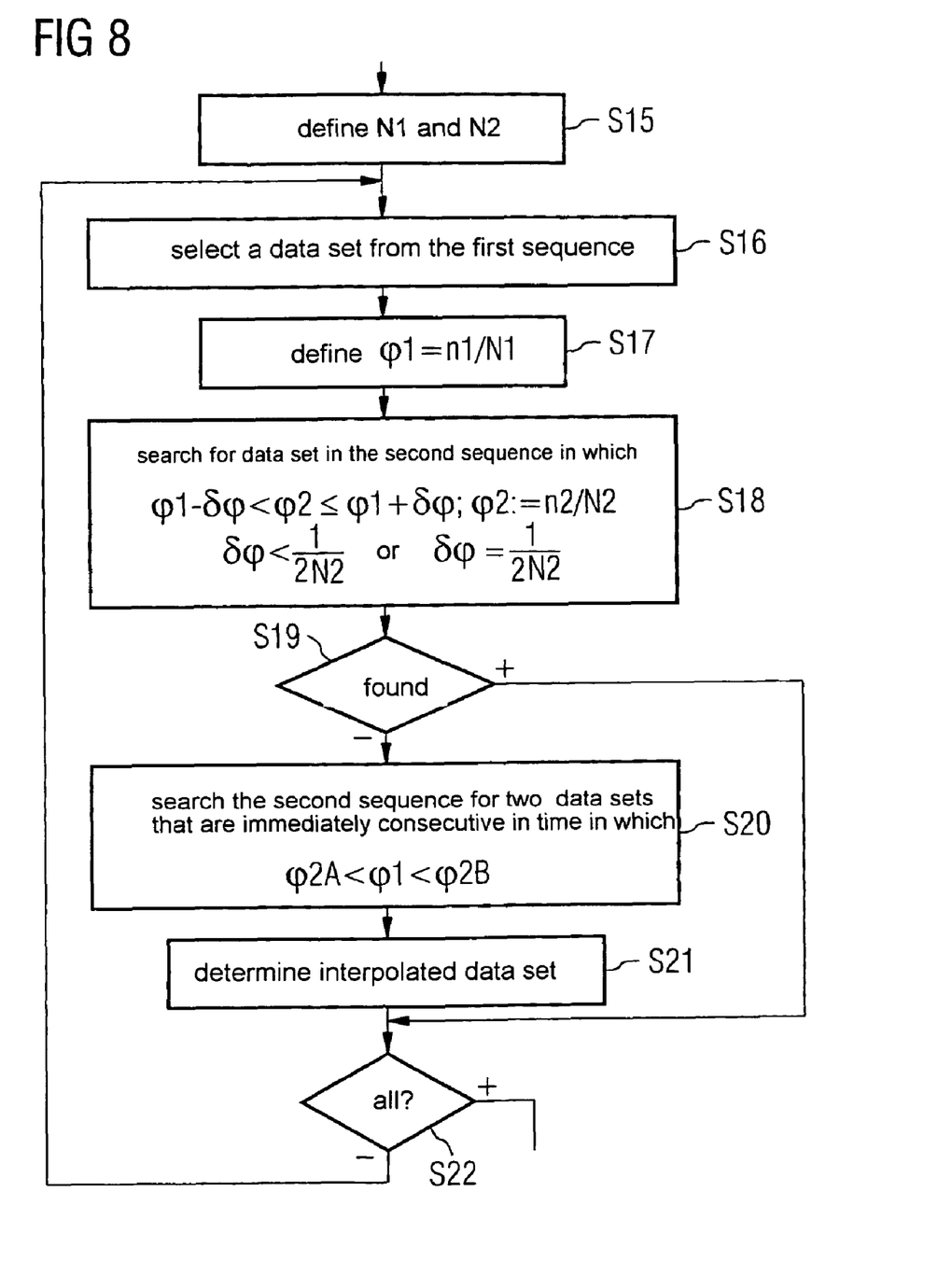

According to FIG. 2 a first data set 14 is selected from the first sequence 13 in a step S2. This selection will be dealt with in greater detail later in conjunction with FIG. 8. In a step S3 the computer 1 uses information other than the measures of time to determine automatically a first data set 16, from the second sequence 15, which corresponds to the first data set 14 in the first sequence 13. With the aid of the pair of data sets 14, 16 determined in the step S3 and the measures of time assigned to the data sets 14, 16, the computer 1 then also determines in a step S4, for each of the other data sets 14 in the first sequence 13, the corresponding data set 16 from the second sequence 15.

After determining the mutually corresponding data sets 14, 16 from the sequences 13, 15 the computer 1 then determines, in a step S5, the registration parameters relating to mutually corresponding data sets 14, 16. In a step S6 it then displays mutually corresponding data sets 14, 16 simultaneously via the output device 6. Alternatively the traces can be displayed side by side or overlaid within one another.

Figure 7:
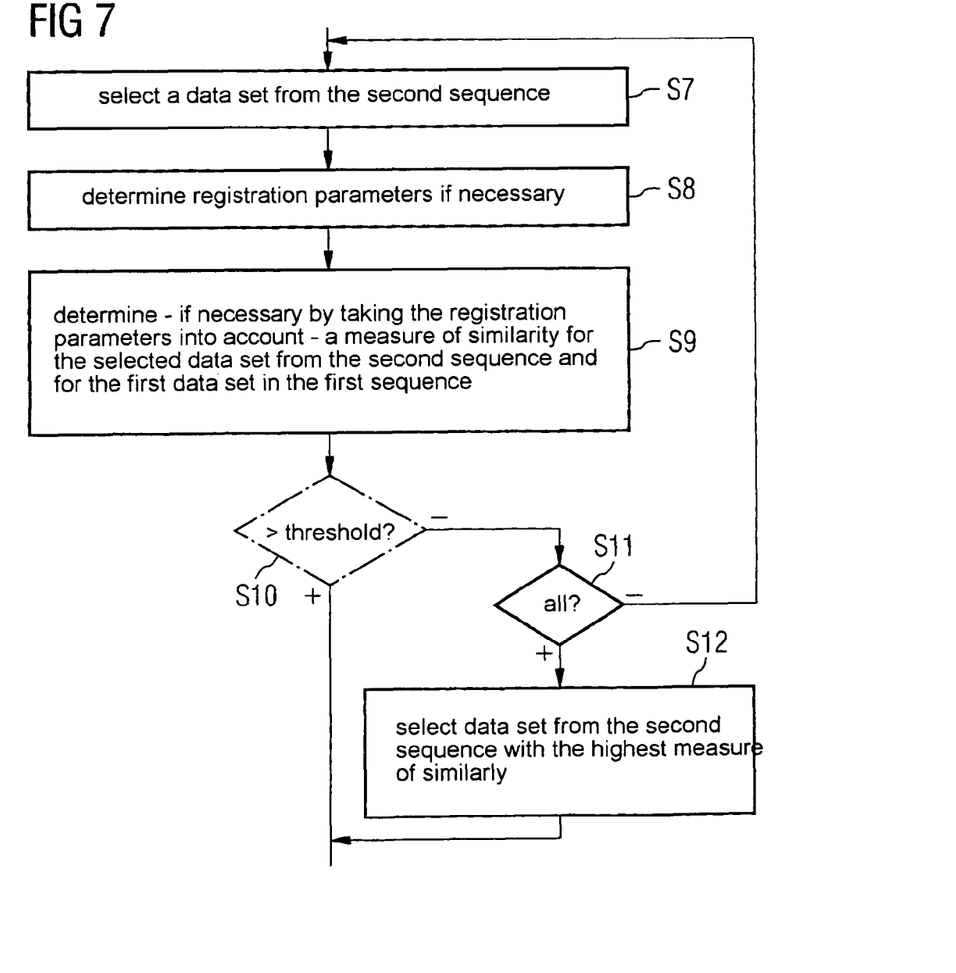

FIG. 7 shows a possible implementation of the step S3 from FIG. 2. According to FIG. 7 it is possible, in a step S7, to initially select a first data set 16 from the second sequence 15 in order to determine the first pair of data sets. In this case the computer 1 also determines if necessary, in a step S8, registration parameters of the first data set 14 in the first sequence 13 and of the data set 16, selected from the second sequence 15 in the step S7, relative to one another. As already mentioned, it is possible for the registration parameters to be determined either fully automatically or interactively. In a step S9 the computer 1 determines a measure of similarity for this pair of data sets 14, 16. If step S8 has been executed, the computer 1 takes into account in step S9 the registration parameters determined in step S8.

From here on there are two possible ways of proceeding.

In the first of these it is possible, as shown by broken lines in FIG. 7, to check in a step S10 whether the measure of similarity determined in step S9 exceeds a predefined threshold. If this is the case, the method described above in connection with FIG. 7 can be terminated. The most recently selected data set 16 from the second sequence 15 then corresponds to the first data set 14 in the first sequence 13. If however the measure of similarity is below the threshold, the method proceeds to step S11. In this step the computer 1 checks whether it has yet selected all the data sets 16 in the second sequence 15. If this is not the case, the computer 1 returns to step S7, where it then selects from the second sequence 15 another data set 16 that has not yet been checked. Otherwise in a step S12 it selects from the second sequence 15 the data set 16 which exhibits the highest measure of similarity.

The step S10 is indicated in FIG. 7 by broken lines only, since it is optional. It can therefore be omitted. In this event the loop consisting of steps S7, S8, S9 and S11 is then executed until all the data sets 16 in the second sequence have been selected once. Step S12 is then executed. The difference between the two methods (with step S10 and without step S10) resides in the fact that in one case, examination of the data sets 16 in the second sequence 15 is terminated as soon as a sufficiently similar data set 16 is found, whereas in the other case the most similar data set 16 from the second sequence 15 is always determined. In both cases, however, the computer 1 determines the corresponding first data set 16 from the second sequence 15 by comparing the first data set 14 from the first sequence 13 with the data sets 16 in the second sequence 15.

As can be seen from FIG. 6, at least some of the data sets 14 in the first sequence 13 are assigned additional information P, which differs from the measure of time. This additional information P characterizes the status of the object 17. As already indicated, if said object 17 is a heart 17, the additional information P may be cardiac current signals which can be used to determine the contraction phases of the heart 17. Similarly it can be seen from FIG. 6 that items of additional information P are also assigned to a plurality of the data sets 16 in the second sequence 15.

FIG. 6 also shows that the object 17 changes with a first period N1 according to the data sets 14 in the first sequence 13, and with a second period N2 according to the data sets 16 in the second sequence 15. In this example, in which the object 17 is a heart 17, the pulse rates recorded for the first sequence 13 differ from those recorded for the second sequence 15. In this case the computer 1 must take the periods N1, N2 in the sequences 13, into account when determining which of the data sets 16 in the second sequence 15 correspond to the various data sets 14 in the first sequence 13. This is explained in detail below by reference to FIG. 9.

Figure 9:
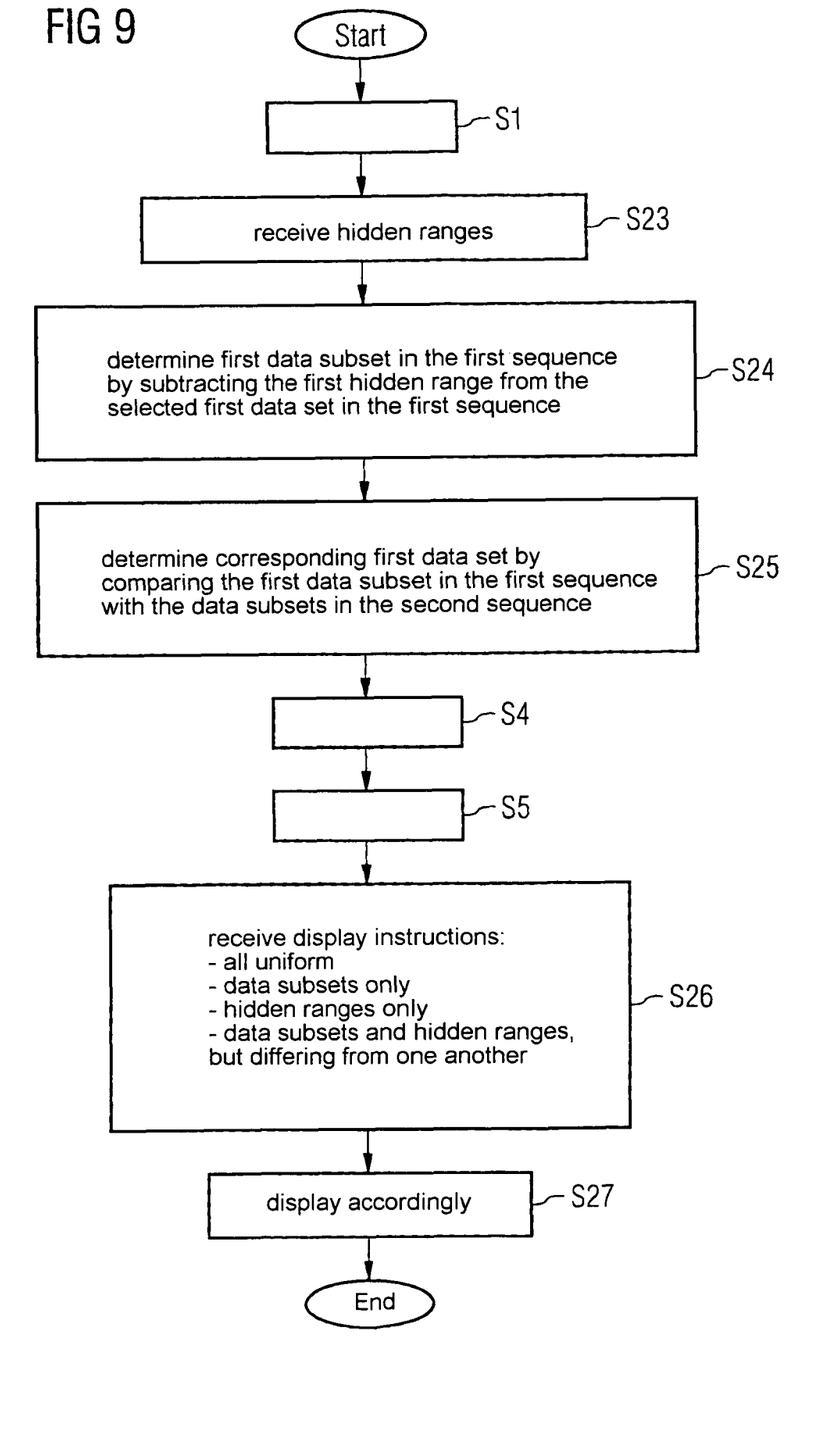

According to FIG. 9, in a step S15 the computer 1 first determines the periods N1, N2. In a step S16 it then selects a data set 14 from the first sequence 13. In a step S17 it goes on to define a time interval n1 between the selected data set 14 and the nearest preceding data set 14 to which the additional information P is assigned together with a corresponding first phase position φ1. By reference to the said data set 14, in a step S18 the computer 1 looks in the second sequence 15 for a data set 16 separated by a time interval n2 from the nearest preceding data set 16 to which the additional information P is assigned. This data set 16 has to fulfill the condition that it must have a second phase position φ2 in which the separation from the first phase position φ1 of the selected data set 14 in the first sequence 13 is not greater than a maximum permitted phase difference δφ. In a step S19 the computer 1 checks whether it can find a data set 16 of this kind in the second sequence 15. If so, said data set 16 in the second sequence 15 has a phase position φ2 relative to the second period N2 that corresponds at least in some respects to the first phase position φ1. In this case the computer 1 is in a position to define this data set 16 as the corresponding data set 16.

If on the other hand the computer 1 cannot find a data set 16 of this kind in the second sequence 15, in a step S20 the computer 1 looks in the second sequence 15 for two data sets 16 that are immediately consecutive in time. These two data sets 16 have second phase positions φ2A and φ2B which bisect the first phase position φ1. The second phase positions φ2A and φ2B are determined in the same way as the second phase position φ2. In this case, by interpolation from these two data sets 16 from the second sequence 15 that are immediately consecutive in time, the computer 1 determines an interpolated data set and defines said interpolated data set as the corresponding data set in the second sequence 15.

In a step S22 the computer 1 then checks whether it has yet executed the sequence of steps from S16 to S21 for all data sets 14 in the first sequence 13. If this is not the case, the computer 1 returns to step S16 and selects another data set 14 from the first sequence 13. Otherwise the process of determining the corresponding data sets 14, 16 is terminated.

The method described above by reference to FIG. 9, in particular the steps S19 to S21, is effective and worthwhile if interpolation from data sets 16 that are immediately consecutive in time in the second sequence 15 is both advisable and feasible. In this case the maximum permitted phase difference δφ is preferably defined so that it is smaller than the reciprocal of twice the second period N2. This is expressed as follows:

$$\delta\varphi < \tfrac{1}{2} N2$$

If on the other hand a true interpolation from immediately consecutive data sets 16 of the second sequence 15 is not desired, the phase difference δφ is preferably set equal to twice the period of the second sequence 15. In this case the maximum permitted phase difference δφ is determined according to the following formula:

$$\delta\varphi = \tfrac{1}{2} N2$$

In this case it is always possible to find in step S18 exactly one data set 16 from the second sequence 15 that fulfills the condition specified in the said step S18. The steps S19 to S21 can therefore be omitted in this case.

A variant of the method according to FIG. 2 and FIG. 7 will now be explained by reference to FIG. 10. The steps S1, S4 and S5 shown in FIG. 10 correspond to those in FIG. 2. These steps will not therefore be described again here. Instead only the other steps appearing in FIG. 10 will be explained, namely steps S23 to S27.

In step S23 the user 12 specifies to the computer 1 hidden ranges 18 for the data sets 14 in the first sequence 13 and hidden ranges 19 for the data sets 16 in the second sequence 15. In step S24 the computer 1 uses the first data set 14 in the first sequence 13 to determine a first data subset 20 by subtracting the hidden range 18. In step S25 the computer 1 uses data subsets 21 in the second sequence 15 to determine a first data set 16 in the second sequence 15. The computer 1 then determines the data subsets 21 in the second sequence 15 by subtracting the second hidden ranges 19 from the data sets 16 in the second sequence 15.

In step S27 the computer 1 receives an item of information from the user 12 defining what the computer 1 must display via the output device 6 and how the display is to be laid out. The information can specify that the computer 1 must display all the data sets 14, 16 in a uniform manner. It is also possible for the computer 1 to be instructed to display only the data subsets 20, 21 or only the hidden ranges 18, 19. It can also be instructed to display the data subsets 20, 21 and the hidden ranges 18, 19 together, but each in a different manner. In step S27 the computer 1 then displays the desired information via the output device 6 in accordance with the specifications in step S26. Here too the information is preferably displayed simultaneously.

The present invention thus makes possible a simple method for registering and merging sequences 13, 15 of images and volume data sets 14, 16. The data sets 14, 16 may originate from the same medical procedure, from similar medical procedures or from medical procedures that differ from one another. For example it is possible to register a sequence of two dimensional recordings of the heart 17 with a four dimensional data set produced by computer tomography. The additional information P in the form of ECG data should also be used in such a case.

The invention claimed is:

1. A method for registering sequences of data sets in a computer of an object having a rate of change represented by a period N of frequency f represented by N=1/f of the rate of change of the object wherein the frequency f corresponds to pulse rate, comprising:

specifying a first sequence of data sets and a second sequence of data sets to the computer wherein the data sets in each sequence are recorded sequences of images or volume data sets of an object, where the object itself changes periodically over time at a frequency f corresponding to pulse rate such that the object itself moves according to a first period N1 of frequency $f_1$ where N1=1/$f_1$ during the first sequence and the object itself moves according to a second period N2 of frequency $f_2$ where N2=1/$f_2$ during the second sequence, and wherein the first and second sequences are images or volume data sets of the same object;

determining the first period of frequency N1=1/$f_1$ of the object and the second period of frequency N2=1/$f_2$ of the object;

assigning a measure of time to each data set in each sequence that is used to determine a temporal relationship of the data set to the other data sets in the respective sequence;

comparing the first data set in the first sequence with the data sets in the second sequence and automatically determining a first data set from the second sequence corresponding to a first data set from the first sequence using registration parameters based on the status of the object that are independent of the measure of time to register the first mutually corresponding pair of data sets in the sequences; and determining for each of the other data sets in the first sequence the mutually corresponding data set from the second sequence based on the first mutually corresponding pair of data sets and the measures of time assigned to the data sets, wherein the temporal relationships of each sequence and periods of frequency N1=1/$f_1$ and N2=1/$f_2$ of the object are taken into account when determining which of the data sets in the second sequence correspond to which of the data sets in the first sequence, wherein the object changes with a first period according to the data sets in the first sequence and with a second period according to the data sets in the second sequence and the computer takes the periods in the sequences into account when determining which of the data sets in the second sequence correspond to the various data sets in the first sequence, and wherein the computer determines a first phase position for each data set in the first sequence relative to the first period in each case and that in each case and for each data set in the first sequence the computer either preferably determines from the second sequence a data set having a second phase position relative to the second period that corresponds at least in some respects, and defines said data set as the corresponding data set or determines two data sets from the second sequence that are immediately consecutive in time and have second phase positions which bisect the first phase position and by interpolation from the two data sets from the second sequence that are immediately consecutive in time determines an interpolated data set which it defines as the corresponding data set.

2. The method according to claim 1, wherein the computer determines registration parameters of the first data set in the first sequence and of the data sets in the second sequence relative to one another and that the computer uses the registration parameters in determining the first data set of the second sequence corresponding to the first data set of the first sequence.

3. The method according to claim 1, wherein the first data set in the first sequence is assigned an additional item of information that differs from the measure of time in that it characterizes the status of the object and that the additional item of information is also assigned to at least one of the data sets in the second sequence.

4. The method according to claim 3, wherein the object is a heart and that the additional information consists of cardiac current signals.

5. The method according to claim 1, wherein the computer determines registration parameters relating to mutually corresponding data sets.

6. The method according to claim 1, wherein the computer displays mutually corresponding data sets simultaneously via an output device.

7. The method according to claim 1, wherein the computer determines the mutually corresponding data sets in the first and second sequences with the aid of subsets of the data sets in the first and second sequences.

8. The method according to claim 7, wherein a user specifies the data subsets to the computer.

9. The method according to claim 8, wherein the user specifies to the computer hidden ranges and the computer determines the data subsets from the data sets by subtracting the hidden ranges.

10. The method according to claim 7, wherein the computer displays mutually corresponding data sets simultaneously via an output device and the computer displays only the data subsets, or only the differences between the data subsets and the data sets, or the data subsets and the differences between the data subsets and the data sets separately from one another.

11. The method according to claim 1, wherein the data sets in the first sequence are images and the data sets in the second sequence are volume data sets.

12. The method according to claim 1, wherein sets in the first sequence are volume data sets and the data sets in the second sequence are images.

13. A computer readable data medium, comprising:

a computer program for executing a method for registering sequences of data sets of an object having a rate of change represented by a period N of frequency f represented by N=1/f of the rate of change of the object wherein the frequency f corresponds to pulse rate, comprising:

specifying a first sequence of data sets and a second sequence of data sets to the computer wherein the data sets in each sequence are recorded sequences of images or volume data sets of an object, where the object itself changes periodically over time at a frequency f corresponding to pulse rate, wherein the object itself moves according to a first period N1 of frequency $f_1$ where N1=1/$f_1$ during the first sequence and the object itself moves according to a second period N2 of frequency $f_2$ where N2=1/$f_2$ during the second sequence, and wherein the first and second sequences are images or volume data sets of the same object;

determining the first period of frequency N1=1/$f_1$ of the object and the second period of frequency N2=1/$f_2$ of the object;

assigning a measure of time to each data set in each sequence that is used to determine a temporal relationship of the data set to the other data sets in the respective sequence;

comparing the first data set in the first sequence with the data sets in the second sequence and automatically determining a first data set from the second sequence corresponding to a first data set from the first sequence using registration parameters based on the status of the object that are independent of the measure of time to register the first mutually corresponding pair of data sets in the sequences; and determining for each of the other data sets in the first sequence the mutually corresponding data set from the second sequence based on the first mutually corresponding pair of data sets and the measures of time assigned to the data sets, wherein the temporal relationships of each sequence and periods of frequency N1=1/$f_1$ and N2=1/$f_2$ of the object are taken into account when determining which of the data sets in the second sequence correspond to which of the data sets in the first sequence, wherein the object changes with a first period according to the data sets in the first sequence and with a second period according to the data sets in the second sequence and the computer takes the periods in the sequences into account when determining which of the data sets in the second sequence correspond to the various data sets in the first sequence, and wherein the computer determines a first phase position for each data set in the first sequence relative to the first period in each case and that in each case and for each data set in the first sequence the computer either preferably determines from the second sequence a data set having a second phase position relative to the second period that corresponds at least in some respects, and defines said data set as the corresponding data set or determines two data sets from the second sequence that are immediately consecutive in time and have second phase positions which bisect the first phase position and by interpolation from the two data sets from the second sequence that are immediately consecutive in time determines an interpolated data set which it defines as the corresponding data set.

14. A computer having bulk storage, comprising:

a computer program stored so that the computer executes a method for registering sequences of data sets of an object having a rate of change represented by a period N of frequency f represented by N=1/f of the rate of change of the object wherein the frequency f corresponds to pulse rate, comprising:

specifying a first sequence of data sets and a second sequence of data sets to the computer wherein the data sets in each sequence are recorded sequences of images or volume data sets of an object, where the object itself changes periodically over time at a frequency f corresponding to pulse rate, wherein the object itself moves according to a first period N1 of frequency $f_1$ where N1=1/$f_1$ during the first sequence and the object itself moves according to a second period N2 of frequency $f_2$ where N2=1/$f_2$ during the second sequence, and wherein the first and second sequences are images or volume data sets of the same object;

determining the first period of frequency N1=1/$f_1$ of the object and the second period of frequency N2=1/$f_2$ of the object;

assigning a measure of time to each data set in each sequence that is used to determine a temporal relationship of the data set to the other data sets in the respective sequence;

comparing the first data set in the first sequence with the data sets in the second sequence and automatically determining a first data set from the second sequence corresponding to a first data set from the first sequence using registration parameters based on the status of the object that are independent of the measure of time to register the first mutually corresponding pair of data sets in the sequences; and determining for each of the other data sets in the first sequence the mutually corresponding data set from the second sequence based on the first mutually corresponding pair of data sets and the measures of time assigned to the data sets, wherein the temporal relationships of each sequence and periods of frequency N1=1/$f_1$ and N2=1/$f_2$ of the object are taken into account when determining which of the data sets in the second sequence correspond to which of the data sets in the first sequence, wherein the object changes with a first period according to the data sets in the first sequence and with a second period according to the data sets in the second sequence and the computer takes the periods in the sequences into account when determining which of the data sets in the second sequence correspond to the various data sets in the first sequence, and wherein the computer determines a first phase position for each data set in the first sequence relative to the first period in each case and that in each case and for each data set in the first sequence the computer either preferably determines from the second sequence a data set having a second phase position relative to the second period that corresponds at least in some respects, and defines said data set as the corresponding data set or determines two data sets from the second sequence that are immediately consecutive in time and have second phase positions which bisect the first phase position and by interpolation from the two data sets from the second sequence that are immediately consecutive in time determines an interpolated data set which it defines as the corresponding data set.

* * * * *